United States Patent
Daridon et al.

(10) Patent No.: US 8,617,287 B2
(45) Date of Patent: Dec. 31, 2013

(54) USE OF A LIQUID MINERAL COMPOSITION FOR IMPROVING THE ADAPTIVE RESPONSE OF PLANTS TO A CHANGE IN ENVIRONMENTAL CONDITIONS

(75) Inventors: Bruno Daridon, Malzeville (FR); Thibaut Veyrier, Corvol L'orgueilleux (FR)

(73) Assignee: PRP Holding, Paris (FR)

(*) Notice: Subject to any disclaimer, the term of this patent is extended or adjusted under 35 U.S.C. 154(b) by 383 days.

(21) Appl. No.: 13/144,189

(22) PCT Filed: Jan. 12, 2010

(86) PCT No.: PCT/FR2010/050042
§ 371 (c)(1), (2), (4) Date: Jul. 12, 2011

(87) PCT Pub. No.: WO2010/081987
PCT Pub. Date: Jul. 22, 2010

(65) Prior Publication Data
US 2011/0271726 A1    Nov. 10, 2011

(30) Foreign Application Priority Data
Jan. 13, 2009  (FR) ..................... 09 50151

(51) Int. Cl.
  *C05C 3/00* (2006.01)
  *C05C 9/02* (2006.01)
  *A01N 25/00* (2006.01)

(52) U.S. Cl.
  USPC ................... 71/61; 71/63; 71/64.1

(58) Field of Classification Search
  USPC ........................................ 71/21–35
  See application file for complete search history.

(56) References Cited

U.S. PATENT DOCUMENTS 3,558,300 A    1/1971  Wagner
4,652,294 A    3/1987  Arnold

FOREIGN PATENT DOCUMENTS

| WO | 91/13844 A1 | 9/1991 |
|---|---|---|
| WO | 2007/060514 A2 | 5/2007 |
| WO | 2007/125531 A2 | 11/2007 |
| WO | 2008/050350 A2 | 5/2008 |
| WO | 2008/145675 A2 | 12/2008 |

OTHER PUBLICATIONS

International Search Report, dated Jun. 20, 2011, from corresponding PCT application.

*Primary Examiner* — Jennifer Smith
(74) *Attorney, Agent, or Firm* — Young & Thompson (57) ABSTRACT

A liquid mineral composition for leaf spraying to improve the adaptive response of plants to a change in environmental conditions. The composition includes the following formula (I) with percentages based on weight per total weight of the composition:

| | |
|---|---|
| total ammoniacal nitrogen (N %) | 0.08% to 2% |
| potassium as $K_2O$ | 3% to 6% |
| magnesium as MgO | 0.4% to 0.8% |
| sodium as $Na_2O$ | 1% to 2% |
| calcium as CaO | 0% to 0.5% |
| total sulphates as $SO_3$ | 3% to 6% |
| total phosphorus as $P_2O_5$ | 0% |
| chlorides Cl | 1% to 2% |
| hydrogen carbonate (% of $HCO_3$) | 1.2% to 3.0% |
| boron | 0.1 to 0.2% |
| copper | 0.018% to 0.03% |
| manganese | 0.00005% to 0.006% |
| iodine | 0.02% to 0.04% |
| zinc | 0.00005% to 0.006% |
| iron (mg/kg) | 0.0002 to 0.003 |
| water | amount sufficient for 100%. |

14 Claims, 7 Drawing Sheets

USE OF A LIQUID MINERAL COMPOSITION FOR IMPROVING THE ADAPTIVE RESPONSE OF PLANTS TO A CHANGE IN ENVIRONMENTAL CONDITIONS

FIELD OF THE INVENTION

The present invention relates to the field of compositions of fertilising substances that preserve or improve the health of plants, useable in agriculture, horticulture, arboriculture or in livestock grassland. It relates more especially to the field of compositions enhancing the defence systems of plants against external biotic or abiotic stresses.

PRIOR ART

The performance of plants, in terms of growth, development, biomass accumulation and yield, depend particularly on their capacity of adaptation to changes in their environmental conditions, which includes events causing physical, chemical and biological stress.

By way of illustration, it has been observed that stressful events such as water stress, osmotic stress or heat stress are limiting factors on plant growth and thus on the level of productivity in the areas of agriculture, horticulture, arboriculture and livestock grassland. Plants exposed to heat or conditions of drought typically have poor yields of plant biomass, seeds, fruit and other products comestible by humans or animals, including livestock. Loss of crops, including loss of yield of exploitable plant material, for example in the culture of rice, maize or wheat, caused by stress events, contributes to food shortages in some developing countries.

Stress events create physiological defence mechanisms in plants that mobilise resources to allow the plant to survive and preserve its health to the detriment of resources used to maintain the initial yield of desired plant material.

In general, a variety of biological or chemical technical solutions are known in the state of the art, designed to protect the plants at least partially from the consequences of external stress events.

Mention can be made particularly of techniques of genetic modification of plants designed to produce transgenic plants with a transmissible characteristic of improves resistance to stress, as disclosed for example in international applications PCT no. WO2007/125531, WO2007/060514, WO2008/050350 and W2008/145675. However, these are specific, long and costly techniques, which must be repeated for each plant variety to be modified genetically. Moreover, in many countries, there exist today general or almost general regulatory bans on cultivating genetically modified varieties of plants in open fields.

According to other ways of solving the problem of the resistance of plants to stress events, today organic or organo-mineral fertilising compositions are marketed, particularly liquid compositions, which are presented for having overall or specific properties to counter deficiencies in nutritive components. Compositions are also known that are designed to stimulate the natural defence reactions of plants to counter stress from pathogenic biological organisms, for example compositions containing substances such as molecules extracted from plants, hydrolysates of agro-polymers, extracts of microorganisms, natural or modified polysaccharides, phytohormones, peptides or proteins or agonistic or antagonistic substances of plant proteins known to be involved in plant defence mechanisms.

The aforementioned compositions can prove satisfactory, particularly for remedying deficiencies in nutritive components or for stimulating plant defences against pathogenic biological organisms such as certain viruses, microorganisms or insects.

However, to the knowledge of the applicant, no purely mineral composition exists that is capable of protecting or stimulating plants against abiotic type stress events, such as conditions of water stress, osmotic stress or heat stress while at the same time contributing to the reaction of plants against chitin-rich attackers such as fungi.

In all instances, given the economic importance and the importance for human or animal food of having healthy plants, particularly plants producing good production yields in agriculture, horticulture, arboriculture and livestock grassland, a need exists in the state of the art for public availability of alternative or improved compositions, at an affordable price, compared with known compositions.

SUMMARY OF THE INVENTION

The present invention relates to the use of a liquid mineral composition, with the formula (I) specified in detail in the rest of the present description, for improving the adaptive response of plants to a change in environmental conditions.

The liquid mineral composition with the formula (I) consists in a concentrated composition which is used, in its form for leaf spraying, in a form diluted in water or in an aqueous liquid.

More particularly, the invention relates to the use of a liquid mineral composition, with the formula (I) disclosed below, for improving the adaptive response of a plant to a biotic or abiotic stress event.

Abiotic stress events include notably water stress, osmotic stress, heat stress, or nutritional deficiency.

Biotic stress events include notably a contact with, or an infection from, biological organisms, including pathogenic microorganisms containing chitin, and substances produced by, or derived from, these various biological organisms, including chitin.

DESCRIPTION OF THE DRAWINGS

FIGS. 2A and 2B show the calcium response curves in ten-day-old plantlets of *Arabidopsis thaliana*, induced by a cold shock, 24 hours after a pre-treatment of the plants in presence or absence of a composition with the formula (I). FIGS. 2A and 2B show the results of two series of identical tests. On the x-axis: the time in seconds. On the y-axis: the concentration of $Ca^{2+}$ ions in the cytosol, in micromoles ($\mu M$).

FIG. 5 shows the long term effects of a composition with the formula (I) on the development of *Arabidopsis thaliana* plantlets previously subjected to different stress events. On the y-axis: measurement of the growth of the plantlets, in centimetres of root growth during the two weeks of applying stress conditions. The block graphs on the x-axis: (a) control plantlets not treated and not subjected to stress; (b) control plantlets not treated subjected to water stress by NaCl; (c) plantlets not treated subjected to osmotic stress with mannitol; (d) plantlets treated with a composition with the formula (I) and not subjected to stress; (e) plantlets treated with a composition with the formula (I) and subjected to water stress by NaCl; (f) plantlets treated with a composition with the formula (I) and subjected to osmotic stress with mannitol.

DETAILED DESCRIPTION OF THE INVENTION

After much research, the applicant has developed a liquid mineral composition which he has shown to have the property of improving the adaptive response of plants to a change in environmental conditions.

Particularly, it is shown that a liquid mineral composition with the formula (I) as defined below in the present description, when used at an appropriate dilution, has the property of improving the adaptive response of plants in reaction to a change in a variety of environmental conditions including water shock, osmotic shock and a defensive reaction when put in contact with certain substances from biological organisms such as fungi.

The present invention thus relates to the use of a liquid mineral composition for leaf spraying comprising the following formula (I):

| | |
|---|---|
| total ammoniacal nitrogen (N %) | 0.08% to 2% |
| potassium expressed as $K_2O$ %. | 3% to 6% |
| magnesium expressed as MgO (%) | 0.4% to 0.8% |
| sodium expressed as $Na_2O$ (%) | 1% to 2% |
| calcium expressed as CaO (%) | 0% to 0.5% |
| total sulphates expressed as $SO_3$ (%) | 3% to 6% |
| total phosphorus expressed as $P_2O_5$ (%) | 0% |
| chlorides Cl (%) | 1% to 2% |
| bicarbonates (% of $HCO_3$) | 1.2% to 3.0% |
| boron (%) | 0.1% to 0.2% |
| copper (%) | 0.018% to 0.03% |
| manganese (%) | 0.00005%-0.006% |
| iodine (%) | 0.02% to 0.04% |
| zinc (%) | 0.00005%-0.006% |
| iron (mg/kg) | 0.0002% to 0.003% |
| water | water in a sufficient amount for 100% | the percentages consisting in percentages by weight compared to the total weight of the composition, for improving the adaptive response of plants to a change in environmental conditions.

The mineral composition with the formula (I) consists in a mineral composition in concentrated form. For use for leaf spraying, the liquid mineral composition with the formula (I) is diluted appropriately in water or in an aqueous liquid.

In order to verify that a composition has the qualitative and quantitative characteristics in mineral components of the compositions with the formula (I), those skilled in the art will refer advantageously to well known assay techniques for this type of composition.

By way of illustration, those skilled in the art can use the following techniques of composition analysis:

(i) for the nitrogen content in the form of ammonia, the technique described by Conway is used (European Community Directive no. 71/393, as amended by European Directives no. 73/47 and no. 81/681), (ii) for the potassium content, the $K_2O$ assay technique is used as per French standard NF U 44-140 and the flame emission technique.

(iii) for the magnesium content, the assay technique described by the French standard no. NF U 44-140 and NF U 44-146 and the atom absorption technique are used, (iv) for the sodium $Na_2O$ content, the assay technique described by the French standard no. NF U 44-140 and the flame photometry technique are used, (v) for the calcium content, the atom absorption spectrometry technique defined in the French standard no. NF U 44-140 and the atom absorption technique are used, (vi) for the total sulphates content, the method defined by the European standard no. CEE 8.1 and the gravimetric technique are used, (vii) for the assay of the total phosphorus expressed as a percentage (weight/weight) of $P_2O_5$, a technique defined by standards NF U 42-241 (CEE 3.1) and NF U 42-246 (spectrophotometry) is used, (viii) for the chloride content, the technique defined by the French standard no. NF U 42-371 is used, (ix) for the bicabonate content, the assay technique for hydrogen carbonate ions according to the technique described in the French standard no. NF EN ISO 9963-1 (T 90-036) is used, (x) for the boron content, the assay technique defined as per the European standard no. CEE 9-1 and no. CEE 9-5 is used, if the final concentration is under 10% (weight/weight), or the European standard no. CEE 10-1 and no. CEE 10-5 if the final concentration is over 10% (weight/weight), (xi) for the copper content, the assay technique defined as per the European standard no. CEE 9-1 and no. CEE 9-7 and the atom absorption technique are used, (xii) for the manganese content, the assay technique defined as per standard no. ICP NF EN ISO 11885 is used, (xiii) for the iodine content, the following technique is used: the sample is reduced to ash as per the Grote-Krekeler preparation method (slide a quartz tube standard DIN 53 474 into small porcelain crucibles). The gaseous iodine is absorbed in caustic soda, then photometric assay is performed using the Sandell-Kolthoff method (with the catalytic influence of the redox couple Ce(IV)/As(III) at 436 nm).

(xiv) for the zinc content, the assay technique defined as per standard ICP NF EN ISO 11885 is used, and (xv) for the iron content, the assay technique defined as per standard ICP NF EN ISO 11885 is used.

In preferred embodiments, the composition with the formula (I) consists in a composition comprising exclusively mineral components or compounds. In these embodiments, the composition with the formula (I) consists in a purely or exclusively mineral composition and consequently contains no organic component or compound, that is no hydrocarbon compound. By way of illustration, composition with the formula (I) contains no vitamins, amino acids, sugars, organic acids or bases, etc.

According to other characteristics, the composition with the formula (I) exists in a concentrated form, which is generally diluted before being used on plants.

In order to produce the composition with the formula (I) above, those skilled in the art will refer advantageously to the technical content of this description, including the examples.

The term "plant" as used herein is understood to mean monocotyledonous and dicotyledonous plants.

Plants, in the sense of the invention, encompass those used for agriculture, for horticulture, for arboriculture and for livestock grassland.

Notably they encompass major crop cereals, fruit trees and flowering plants. The plants notably encompass wheat, barley, oilseed rape, maize and rice and the tree species such as apple, pear, plum, peach and apricot trees.

Dicotyledons encompass the following species and families: Nymphaeaceae, Ceratophyllaceae, Ranunculaceae, Papaveraceae, Fumariaceae, Ulmaceae, Cannabinaceae, Urticaceae, Myricaceae, Fagaceae, Betulaceae, Aizoaceae, Chenopodiaceae, Portulacaceae, Caryophyllaceae, Polygonaceae, Plumbaginaceae, Elatinaceae, Guttiferae/Hypericaceae/Clusiaceae, Malvaceae, Malvaceae, Droseraceae, Violaceae, Cucurbitaceae, Salicaceae, Cruciferae/Brassicaceae, Resedaceae, Empetraceae, Ericaceae, Pyrolaceae, Monotropaceae, Primulaceae, Grossulariaceae, Crassulaceae, Saxifragaceae, Rosaceae, Leguminosae/Fabaceae, Elaeagnaceae, Halogaraceae, Lythraceae, Onagraceae, Viscaceae, Celastraceae, Aquifoliaceae, Euphorbiaceae, Rhamnaceae, Linaceae, Polygalaceae, Aceraceae, Oxalidaceae, Geraniaceae, Balsaminaceae, Araliaceae, Umbelliferae/Apiaceae, Gentianaceae, Apocynaceae, Solanaceae, Convolvulaceae, Cuscutaceae, Menyanthaceae, Boraginaceae, Lamiaceae, Hippuridaceae, Callitrichaceae, Plantaginaceae, Buddlejaceae, Oleaceae, Scrophulariaceae, Orobanchaceae, Lentibulariaceae, Campanulaceae, Rubiaceae, Caprifoliaceae, Adoxaceae, Valerianaceae, Dipsacaceae and Compositae/Asteraceae.

The term "adaptive response" of a plant as used herein is understood to mean any detectable physiological modification of a plant after applying a rapid change of environmental conditions to said plant. The detectable physiological modifications encompass any modification in the quantity or concentration of one or several tissue metabolites, including intracellular metabolites or any detectable qualitative or quantitative modification of enzymatic activities of said plant, or any detectable modification in the morphology of said plant. The adaptive responses of plants notably lead to the production by plant cells of metabolites known as "second messengers". Second messengers encompass calcium ions, and reactive oxygen species (ROS).

The "environmental conditions" encompass water conditions, salinity conditions, osmotic conditions, oxidative conditions and thermal conditions. A rapid change in the environmental conditions of the plant is also called a "shock" or "stress" in the present description. Environmental conditions encompass (i) "biotic" conditions that are the result of the biological environment of the plant and (ii) "abiotic" conditions that are the result of the physical and chemical environment of the plant.

The changes in environmental conditions consisting in abiotic stress or shock encompass salt, osmotic, oxidative, heat and water stress or shocks and shocks caused by the plant being in contact with toxic substances such as certain metals or certain synthetic organic toxic chemical substances or certain natural or synthetic mineral substances. They also encompass exposure to ionising or non-ionising radiation and a deficit or excess of nutrients.

Salt stress or shock can be caused when the plant grows on a soil with high sodium chloride level, for example in coastal fields or meadows. Salt stress leads notably to a deregulation of homeostasis and ion distribution in the plant tissues, which leads to an alteration of seed germination and plant growth.

Osmotic stress or shock can also be provoked artificially by growing on a mannitol-rich substrate. Osmotic stress leads notably to a deregulation of homeostasis and ion distribution in the plant tissues, which leads to an alteration of seed germination and plant growth.

Oxidative stress or shock can be provoked artificially by growing on methyl viologen. Oxidative stress notably causes the formation of reactive oxygen species (ROS), protein denaturing and chlorophyll degradation, which leads to a bleaching of the plant and can lead to its death.

Heat stress or shock encompasses stress caused by heat and stress caused by cold. Stress provoked by growing at high temperature notably causes denaturing of proteins, which leads to an alteration of plant growth. Stress provoked by growing in the cold notably causes the formation of reactive oxygen species, and rupture of cell membranes, which leads to an alteration of plant growth.

Water stress can be provoked by growing in dry conditions. Water stress notably causes a repression of cell growth and photosynthesis, which leads to en alteration of plant growth.

Changes in environmental conditions consisting in biotic stress or shock encompass stresses or shocks caused by putting the plant in contact with unicellular or multi-cellular organisms, for example bacteria, viruses, fungi, plant-eating organisms, insects or pathogenic organisms, or stresses or shocks caused by putting the plant in contact with substances originating from unicellular or multicellular organisms. Biotic stress can be caused by bacteria, viruses or fungi or parts of these, or substances of bacterial, viral or fungal origin.

A composition with the formula (I) according to the invention has the property of directly inducing a physiological pathway involved in the adaptive response of plants to a change in environmental conditions, notably the induction of a calcium signalling pathway, as illustrated by the effect of the increase in the concentration of $Ca^{2+}$ ions which is shown in the examples. Thus, a composition with the formula (I) induces calcium variations in the cytosol of cells, the level of which depends on the quantity of composition with the formula (I) which has been put in contact with the plant.

It has also been shown that the composition with the formula (I) induces changes in the response of plants to abiotic stress such as a cold shock.

Equally, the results presented in the examples show that a composition with the formula (I) according to the invention is capable of stimulating an increase in the production of hydrogen peroxide ($H_2O_2$) in reaction to the application of osmotic stress.

Thus, in certain of its aspects, the improvement of the adaptive response of plants which is brought about by the composition with the formula (I), in the meaning of the present invention, encompasses:
(i) the property of increasing detectably the calcium response of plants to abiotic or biotic stress, the increase of the calcium response being detected by measuring the concentration of $Ca^{2+}$ ions in the plant tissue, and especially in the cytosol of plant cells; and
(ii) the property of increasing detectably the production of hydrogen peroxide in the plant tissue in response to abiotic or biotic stress.

The fact that the composition with the formula (I) according to the invention has the property of increasing the plant's calcium response in reaction to biotic or abiotic stress is important, because the calcium ions produced at the time of the calcium response are known in the state of the art as species called "second messengers" in the signalling pathways located metabolically and chronologically very high up in the cascade process that leads to the induction of the adaptive responses of the plant that has been subjected to biotic or abiotic stress. It is known that the increase in the calcium ion concentration causes the activation of proteins with affinity for these ions, such as calciproteins. Then the activated calciproteins in turn activate other enzymatic activity proteins, such as kinases, or activate other non-enzymatic proteins, such as "pump" proteins (Sanders, D., Brownlee, C., and Harper, J. F. (1999). Communicating with calcium. Plant Cell 11, 691-706. Shapiro, A. D. (2005). Nitric oxide signaling in plants. Plant Hormones VOL 72, 339-398; Brownlee, C. (2003). Plant signalling: Calcium first and second. Current Biology 13, R923-R924, Hetherington, A. M., and Brownlee, C. (2004). The generation of $Ca^{2+}$ signals in plants. Annu Rev Plant Physiol Plant Mol Biol 55, 401-427; Harper, J. F., Breton, G., and Harmon, A. (2004). Decoding $Ca^{2+}$ signals through plant protein kinase. Annu Rev Plant Biol 55, 263-288; Mori, I. C., Murata, Y., Yang, Y. Z., Munemasa, S., Wang, Y. F., Andreoli, S., Tiriac, H., Alonso, J. M., Harper, J. F., Ecker, J. R., Kwak, J. M., and Schroeder, J. I. (2006). CDPKs CPK6 and CPK3 function in ABA regulation of guard cell S-type anion- and $Ca^{2+}$-permeable channels and stomatal closure—art. no. e327. Plos Biology 4, 1749-1762; George, L., Romanowsky, S. M., Harper, J. F., and Sharrock, R. A. (2007). The ACA10 $Ca^{2+}$ ATPase Regulates Adult Vegetative Development and Inflorescence Architecture in *Arabidopsis*. Plant Physiol.). These cascade processes help develop the plant's specific adaptive responses, in reaction to the initial stress. As examples of adaptive responses of plants, mention can be made of stomatal closure which limits water loss during periods of water stress, the production of protective osmolytes in reaction to a heat or osmotic stress, and the production of endogenous toxic substances which have the effect of limiting the progression of pathogenic organisms.

The fact that the composition with the formula (I) according to the invention has the property of increasing the plant's oxidative response, especially the production of reactive oxygen species, in reaction to biotic or abiotic stress is important. More specifically, it is particularly advantageous that a composition with the formula (I) according to the invention notably brings about an increase in hydrogen peroxide production, which is the most stable reactive oxygen species and therefore, as a "second messenger" compound, can remotely induce the cellular reactions needed to produce the plant's reactive response. It should be remembered that the production of reactive oxygen species causes the triggering of most of the adaptive responses of plants to abiotic stress. It should also be specified that the adaptive responses of plants in reaction to biotic or abiotic stress bring about the production of reactive oxygen species encompassing: thermal dissipation of excess energy, photochemical dissipation of energy using oxygen as the electronic transport chain acceptor, the use of a whole series of antioxidant enzymes and molecules to detoxify the ROS produced, the involvement of antioxidant enzymes (superoxide dismutase, catalase, glutathione peroxidases, ascorbate peroxidase, thioredoxin/thioredoxin reductase couple, heat shock proteins), the involvement of iron- and copper-carrying proteins (transferrin, ferritin), involvement of small antioxidant molecules: glutathione, carotenoids, vitamins A, C (ascorbic acid), E (tocopherol), ubiquinone, flavonoids, bilirubin, and involvement of oligoelements (copper, zinc, selenium) which are vital as cofactors for antioxidant enzymes activity.

Thus, in one of these aspects, the use of the composition with the formula (I) is characterised in that it improves the adaptive response of plants to biotic or abiotic stress.

In certain embodiments, the use of the composition with the formula (I) is characterised in that abiotic stress is chosen from among water stress, osmotic stress, heat stress, or nutritional deficiency. Nutrient deficiencies encompass mineral deficiencies, including deficiencies in oligoelements.

According to other embodiments, the use of the composition with the formula (I) is characterised in that biotic stress includes notably a contact with, or an infection from, biological organisms, including pathogenic microorganisms containing chitin, and substances produced by, or derived from, these various biological organisms, including chitin.

Furthermore, the applicant has also shown according to the invention that the composition with the formula (I), notably by application to leaves, has the property of stimulating plant root growth, both of plants placed in normal growing conditions and plants to which at least one abiotic or biotic stress condition has been applied.

Thus, in still other aspects, the use according to the invention is characterised in that the composition with the formula (I) also leads to an increase in plant root development. The increase in root development can be demonstrated by an increase in the speed of root growth, by measuring the average length.

Thus the composition with the formula (I) combines (i) an effect of increasing the adaptive response of plants to a change in environmental conditions and (ii) and a physiostimulant effect demonstrated by the effect on increased root development.

Thus it is shown according to the invention that the composition with the formula (I), when it is applied to plants, preferably by dispersion on leaves, brings about the following technical effects:
   an increase in the calcium response of plants to water stress, osmotic stress and heat stress,
   an increase in the elicitation reaction of plant defence mechanisms by the chitin elicitor,
   an improvement in the oxidative status of plant cells, by stimulation of the production of reactive oxygen species, including hydrogen peroxide ($H_2O_2$),
   an increase in the speed of root growth of young plants, and
   an increase in the resistance of young plants to drought.

Particularly, the following effects of the composition with the formula (I) are shown in the examples:

A. At the Level of the Second Messengers of Plant Response to Biotic/Abiotic Stress ($Ca^{2+}$ and $H_2O_2$) Involved in Signalling Pathways:
   a) The composition with the formula (I) is perceived by plants as an exogenous stimulus induced by signalling pathways involving cytosolic calcium variations in the cells of *Arabidopsis thaliana* plantlets. Treatment with the composition with the formula (I) induces changes in the plant's ability to respond to stress.
   b) The production of reactive oxygen species such as ($H_2O_2$) in response to the chitin elicitor in plantlets pre-treated with the composition with the formula (I) is higher than that measured in plantlets sprayed with water. This result indicates an increase of the defence reactions of plants pre-treated with the composition with the formula (I) in response to the elicitors produced by pathogenic agents.

B. At the Level of the Growth and Development of Plantlets:
   a) The composition with the formula (I) significantly increases the root growth of plantlets of *Arabidopsis thaliana* in normal conditions or in conditions of (osmotic or salt) stress.

b) The recovery or development of plantlets subjected to an intense water stress, is improved by prior treatment with the composition with the formula (I).

The results in the examples thus show that the composition with the formula (I) has a beneficial effect on the growth and development of plantlets, both in normal growing conditions and in stress conditions.

In certain advantageous embodiments, the composition of the invention has the following formula (II), which is encompassed by formula (I):

| | |
|---|---|
| total ammoniacal nitrogen (N %) | 0.08% to 1% |
| potassium expressed as $K_2O$ (%) | 3.5% to 4.5% |
| magnesium expressed as MgO (%) | 0.4% to 0.5% |
| sodium expressed as $Na_2O$ (%) | 1.2% to 1.6% |
| calcium expressed as CaO (%) | 0% to 0.1% |
| total sulphates expressed as $SO_3$ (%) | 3% to 5% |
| total phosphorus expressed as $P_2O_5$ (%) | 0% |
| chlorides Cl (%) | 1% to 2% |
| bicarbonates (% of $HCO_3$) | 1.5% to 1.9% |
| boron (%) | 0.1% to 0.15% |
| copper (%) | 0.020% to 0.026% |
| manganese (%) | 0.00005% to 0.0002% |
| iodine (%) | 0.025% to 0.031% |
| zinc (%) | 0.00005% to 0.0002% |
| iron (%) | 0.0002% to 0.001% |
| water | water in a sufficient amount for 100% | where the percentages consist in percentages by weight compared with the total weight of the composition.

In still other advantageous embodiments, the composition of the invention has the following formula (III), which is encompassed by each of the formulas (I) and (II):

| | |
|---|---|
| total ammoniacal nitrogen (N %) | 0.09% |
| potassium expressed as $K_2O$ (%). | 4% |
| magnesium expressed as MgO (%) | 0.45% |
| sodium expressed as $Na_2O$ (%) | 1.40% |
| calcium expressed as CaO (%) | 0.05% |
| total sulphates expressed as $SO_3$ (%) | 3.85% |
| total phosphorus expressed as $P_2O_5$ (%) | 0% |
| chlorides Cl (%) | 1.40% |
| bicarbonates (% of $HCO_3$) | 1.7% |
| boron (%) | 0.12% |
| copper (%) | 0.023% |
| manganese (%) | 0.00005% |
| iodine (%) | 0.028% |
| zinc (%) | 0.00005% |
| iron (%) | 0.0003 |
| water | water in a sufficient amount for 100% | where the percentages consist in percentages by weight compared with the total weight of the composition.

A further object of this invention is also any of the compositions disclosed in the present description, including the examples, and notably the compositions with formulas (I), (II) and (III).

In certain embodiments, a composition with the formula (I) can be obtained according to the protocol specified in the table below

| | |
|---|---|
| tap water | water in a sufficient amount for 100% |
| potassium iodide | 0.030 to 0.050% |
| sodium chloride | 0.8 to 1.2% |
| boric acid | 0.6 to 1.0% |
| sodium carbonate | 2.0 to 4.0% |
| magnesium chloride | 2.0 to 4.0% |
| potassium sulphate | 7.0 to 1.10% |
| copper sulphate pentahydrate | 0.05 to 0.15% |
| ammonium sulphate | 1.5 to 3.5% |

The percentages above consist in percentages by weight for each ingredient, compared with the total weight of the liquid composition.

The various ingredients above are added to tap water, at ambient temperature, then the solution obtained is mixed vigorously until a stable liquid composition is obtained. The liquid composition is then filtered to eliminate undissolved solids, in order to obtain a clear ready-to-use composition with the formula (I).

Advantageously, the composition with the formula (I), including its specific example with the formula (II), consists in a liquid formulation in concentrated form, which is diluted in a certain volume of water in order to obtain a diluted ready-to-use composition.

Thus, the invention also relates to the use of a liquid mineral composition for leaf spraying consisting in a concentrated composition with the formula (I), including a composition with the formula (II), which has been diluted in 50 to 10000 times its volume of water, preferably 100 to 5000 times its volume of water, for example 100 to 1000 times or 400 to 600 times its volume of water, to improve the adaptive response of plants to a change in environmental conditions.

The present invention also relates to the use of a concentrated mineral composition with the formula (I) characterised in that, before leaf spraying, the composition with the formula (I) is diluted in water in a proportion Composition (I):water or aqueous liquid ranging from 0.1:500 (V/V) to 10:500 (V/V), preferably ranging from 0.5:500 (V/V) to 2:500 (V/V).

In practice, the above diluted composition is advantageously applied to plants by dispersion on the aerial parts of the plant, preferably by leaf spraying.

In certain embodiments, the above diluted composition is applied by dispersion on the aerial parts of plants in quantities ranging from 0.5 l to 20 l per hectare of plant surface to be treated, preferably 1 l to 10 l per hectare of plant surface to be treated, per period of one year, in one or several fractions.

Furthermore, the present invention is illustrated, without being in any way limited, by the following figures and examples.

EXAMPLES

A. Materials and Methods for Examples

A.1 Plant Material

Plantlets of *Arabidopsis thaliana* ecotype Col 0 (wild) or ecotype No0 (transgenic expressing the aequorin calcium probe) aged 10 days.

The plantlets are cultivated either in vitro in Petri dishes on nutritive agar (Murashige and Skoog MS medium), or on potting soil in pots or in Jiffy pots.

For cultivating the plantlets in vitro, previously sterilised seeds of *Arabidopsis thaliana* are sown in lines of approximately 100 seeds.

A.2. Measuring the Calcium Response of *Arabidopsis thaliana* Plantlets

The day before the measurements, 50 approximately 10-day-old plantlets are collected from an in vitro culture and put into Petri dishes in threes in 500 μl of water containing 2

μM of coelentarazine, then incubated in the dark at ambient temperature overnight. The next day, the measurements are made with a luminometer by transferring a batch of 3 plantlets into a Petri dish containing 1 ml of solution of composition with the formula (III) at the chosen concentration and by recording the signal emitted by the aequorin after putting the plantlets in contact (by immersion) with the product. After recording the signal for 15 min, the aequorin is removed by injecting a lysis solution containing 100 mM CaCl$_2$ in order to calibrate the signal.

A.3. Measuring the H$_2$O$_2$ Production of *Arabidopsis thaliana* Plantlets

The production of H$_2$O$_2$ by 10-day-old *Arabidopsis thaliana* plantlets was measured by the luminescence produced by the oxidation of luminol. Batches of 3 plantlets were placed in Petri dishes in the luminometer, then the luminescence was measured for 10 min after injection of the reaction medium (20 μM luminol, 4 units of peroxidase, 5 mM Tris-HCL pH 7.8) supplemented either with 350 mM mannitol, or with 10 μg/ml chitin, used here as a positive control capable of inducing H$_2$O$_2$ production.

A.4. Measurement of the Root Growth of Plantlets Cultivated In Vitro Pre-Treated with a Composition with the Formula (I)

For each test, a line of 10-day-old plantlets was treated by spraying with the composition with the formula (III) at 2% then transferred either to a normal medium or to a stress inducing medium (100 mM NaCl or 350 mM Mannitol). Then root growth was followed daily.

A.5. Observation of the Development of *Arabidopsis thaliana* Plantlets in Stress Conditions after Pre-Treatment with a Composition with the Formula (I)

*Arabidopsis thaliana* seeds were sown in pots on potting soil then cultivated in a phytotron (t°=22/20° C., photoperiod 9/15, 70% moisture) for 10 days (*A. thaliana*).

The young plantlets were then treated by spraying the leaves with water (controls) or with the composition with the formula (III) at 2% in water, then they were placed in stress conditions: osmotic stress (daily watering with 350 mM mannitol), salt stress (watering with 100 mM NaCl) or water stress (no watering).

Then development of the plantlets was then followed daily by photography.

Example 1

Preparing a Composition with the Formula (I)

A composition with the formula (I) was prepared with the following formula (III):

| | |
|---|---|
| total ammoniacal nitrogen (N %) | 0.09% |
| potassium expressed as K$_2$O (%). | 4% |
| magnesium expressed as MgO (%) | 0.45% |
| sodium expressed as Na$_2$O (%) | 1.40% |
| calcium expressed as CaO (%) | 0.05% |
| total sulphates expressed as SO$_3$ (%) | 3.85% |
| total phosphorus expressed as P$_2$O$_5$ (%) | 0% |
| chlorides Cl (%) | 1.40% |
| hydrogen carbonate (% of HCO$_3$) | 1.7% |
| boron (%) | 0.12% |
| copper (%) | 0.023% |
| manganese (%) | 0.00005% |
| iodine (%) | 0.028% |
| zinc (%) | 0.00005% |
| iron (%) | 0.0003 |
| water | water in a sufficient amount for 100% | where the percentages consist in percentages by weight compared with the total weight of the composition.

The composition with the formula (III) was prepared according to the protocol summarised in the table below.

| Ingredients | Quantity of salt (g) | Final concentration of salt added (g/l) |
|---|---|---|
| Tap water | 2 500.00 | |
| KI | 1.00 | 0.40 |
| NaCl | 24.00 | 9.60 |
| H$_3$BO$_3$ | 20.00 | 8.00 |
| NaHCO$_3$ | 72.50 | 29.00 |
| MgCl$_2$ | 65.00 | 26.00 |
| K$_2$SO$_4$ | 247.50 | 99.00 |
| CuSO$_4$•5H$_2$O | 2.50 | 1.00 |
| (NH$_4$)$_2$SO$_4$ | 62.50 | 25.00 |
| TOTAL | 495.00 | 198.00 |

The various ingredients were added to tap water, at ambient temperature, then the solution was mixed vigorously until a stable liquid composition was obtained.

The liquid was then filtered to obtain the clear stable ready-to-use soluble composition with the formula (III). For filtering, the ashless cellulose filter paper PRAT DUMAS® with a pore size ranging from 7 to 10 micrometres can be used.

In the following examples, the composition with the formula (III) was used at different dilutions ranging from 0.01% to 8.00% (volume/volume) in tap water, and the resulting diluted composition was used for spraying leaves.

Example 2

Measuring the Calcium Response of *Arabidopsis thaliana* Plantlets to the Application of a Composition with the Formula (I) to its Leaves The applicant has shown that the application of the composition with the formula (III) brings about calcium variations in the cells which proves that the composition with the formula (III) is perceived by the plant as a stimulus that leads to adaptive responses in the plant.

Figure 1A:
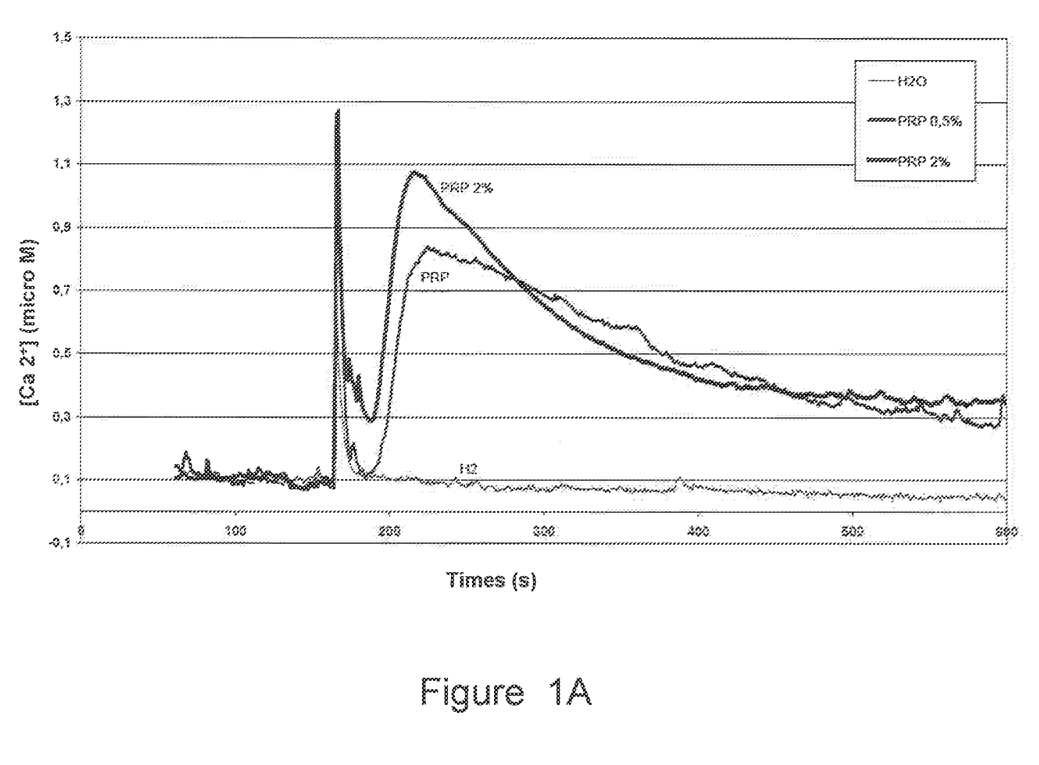
FIGS. 1A and 1B show the calcium response curves in ten-day-old plantlets of *Arabidopsis thaliana*, induced by treatment with increasing quantities of a composition with the formula (I). On the x-axis: the time in seconds. On the y-axis: the concentration of $Ca^{2+}$ ions in the cytosol, in micromoles ($\mu M$).
Figure 1B:
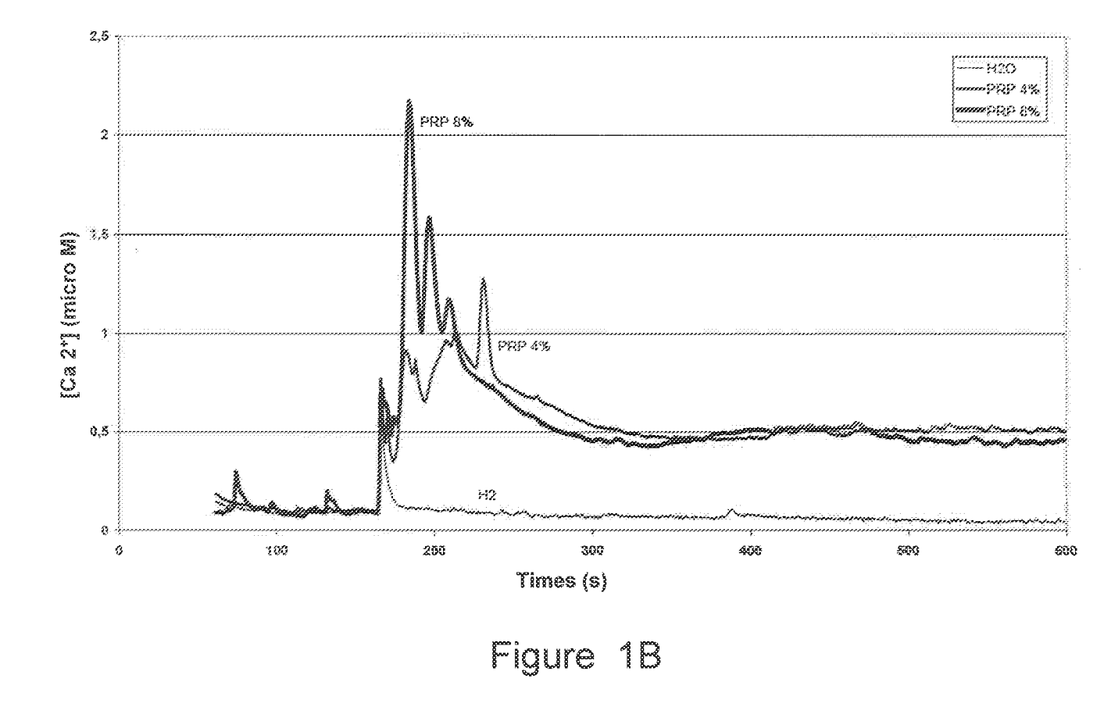

The results are presented in FIGS. 1A and 1B, which show the calcium variations brought about in the 10-day-old *Arabidopsis thaliana* plantlets by different concentrations of the composition with the formula (III) (arrow=time of contact of the plantlets with the product).

In order to do this, *Arabidopsis thaliana* plantlets expressing the gene for aequorin in the cytosol were used. Dilutions of 0.01 to 8% (V/V) of the composition with the formula (III) in water were tested and a control with water was run. When the plantlets were put in contact with the solution, a rapid signal variation was observed that is attributable to the manipulation itself (mechanical shocks) and independent from the product concentration (it was also observed with the water controls).

The results show that the composition with the formula (III) leads to a bi-modal dose-dependent calcium response, with a peak between 30 seconds and one minute after putting the plantlets in contact with the product, followed by a phase of progressive return to the base level for dilutions below 2% (V/V), or an extended plateau for dilutions above 2% (V/V). It should be noted that above a concentration of 2% (V/V) of the composition with the formula (III), the calcium response is rapid, intense and with high background noise.

Therefore it can be concluded from these tests that:
1) The composition with the formula (III), even highly diluted to 0.01% (V/V), has a stimulatory effect on the calcium response of plants. The product brings about calcium variations in the cell cytosol that varies with the concentration, and thus the quantity, of the composition with the formula (III) that is applied to the leaves.
2) For concentrations over 2% (V/V), this calcium response has different characteristics from that obtained for concentrations under 2%. For concentrations over 2% (V/V), the calcium response notably has a large plateau phase (delta $[Ca^{2+}]>0.5\%$), which could imply different final biological responses to these "second messenger" calcium signals.

Example 3

Study of the Long Term Effect of Leaf Application of a Composition with the Formula (I) on the Calcium Response of *Arabidopsis thaliana* Plantlets to a Cold Shock To determine the effect of pre-treatment of *Arabidopsis thaliana* plantlets with the composition with the formula (III) on the calcium response brought about by cold shock, 10-day-old plantlets were sprayed the day before measurements with a 2% solution of the composition with the formula (III) or with water (control). Approximately three hours after treatment, these plantlets were collected and put to incubate in coelentarazine overnight, as described in Material and Methods. The next day the calcium responses brought about in these plantlets by the cold shock were recorded.

The cold shock, obtained by immersing the plantlets in water at 4° C. is known to cause a rapid, intense and short-lived calcium response.

Figure 2A:
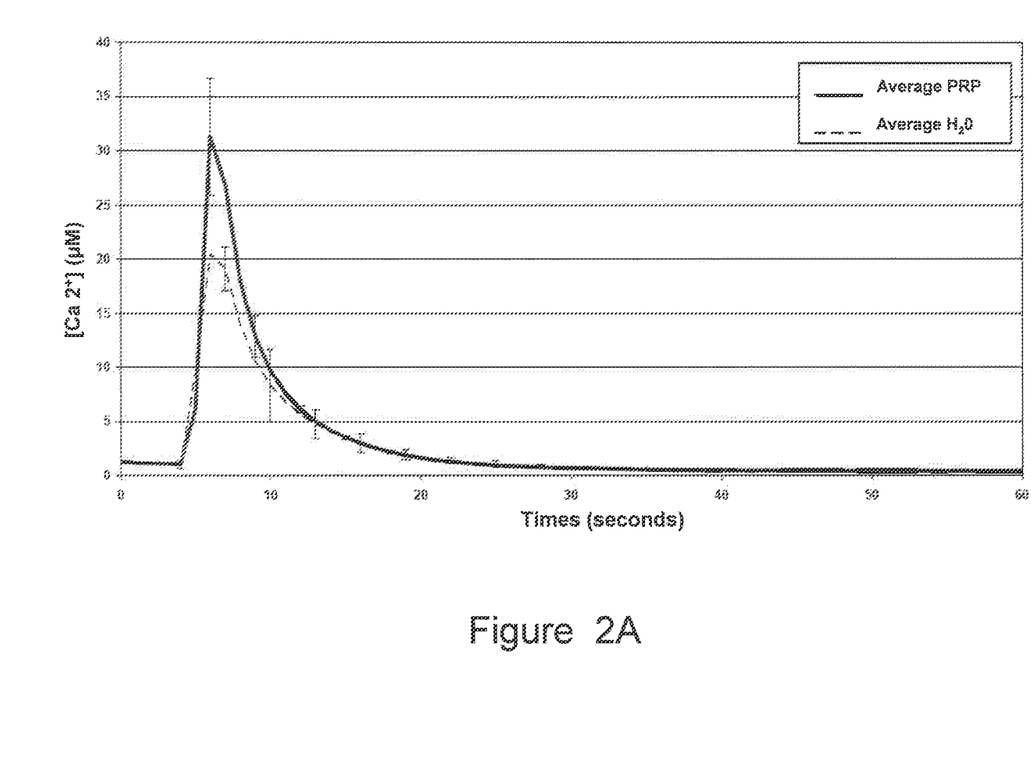
Figure 2B:
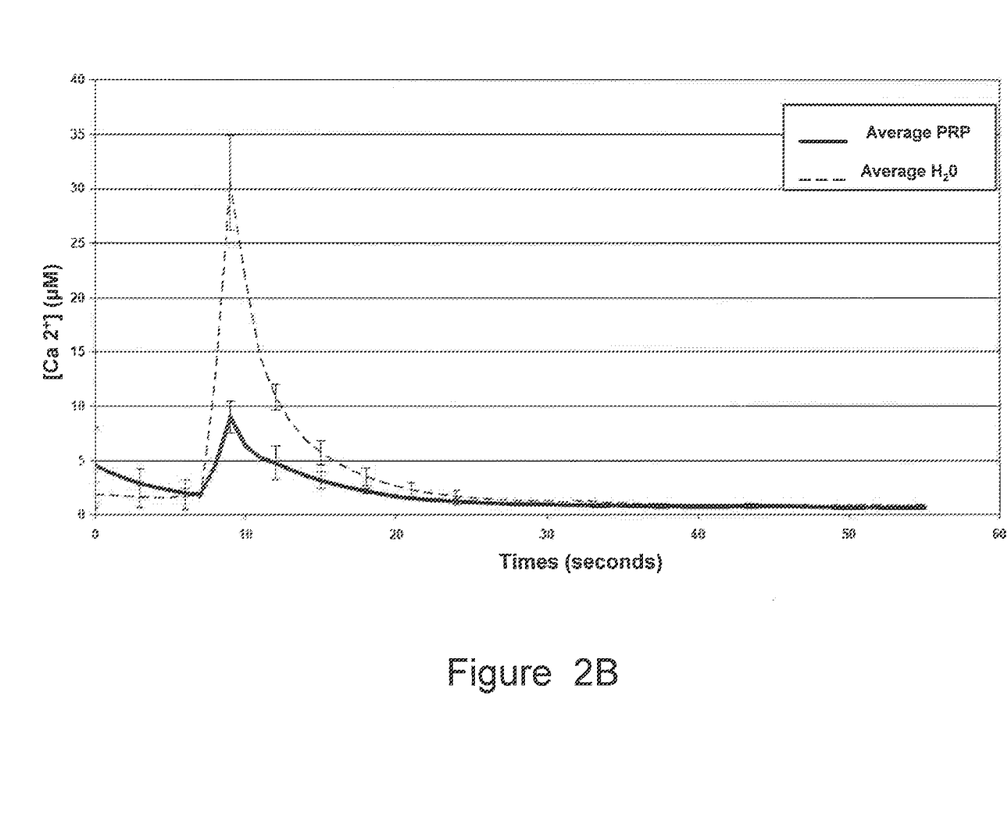

FIGS. 2A and 2B show the average results obtained in two series of independent experiments in triplicate, 24 and 48 hours after pre-treatment with a composition with the formula (III).

After 24 hours, a significant difference was observed in the intensity of the response caused by the stress depending on the pre-treatment (composition with the formula (III) or water).

It is shown that the treatment with the composition with the formula (III) significantly increases the response to cold.

In the second series of tests, the treatment with the composition with the formula (III) causes a significant desensitisation to cold compared with the plants treated with water.

Depending on the test considered, the composition with the formula (III) thus has either an amplifying or an inhibiting effect on the response which does not enable conclusions to be drawn on its effect. After 48 hours on two series of experiments, it was apparent that the PRP treatment could no longer be distinguished from water treatment (control).

In conclusion, the results of example 3 show that pre-treatment with a composition with the formula (III) at 2% (V/V) brings about a change of behaviour in plants in the calcium response to cold shock if the latter is applied within a maximum delay of 24 hours.

Example 4

Study of the Long Term Effect of a Composition with the Formula (I) on the Production of $H_2O_2$ in *Arabidopsis thaliana* Plantlets in Response to an Osmotic Shock or to an Elicitor Treatment by a Substance Produced by a Pathogenic Organism In example 4, the aim was to determine the effect of pre-treatment of *Arabidopsis thaliana* plantlets with the composition with the formula (III) on the $H_2O_2$ response brought about by osmotic shock or by an elicitor substance produced by a fungal microorganism, the chitin. Chitin is used here as a positive control known to bring about $H_2O_2$ production and mimic stress caused by pathogenic agents able to bring about defence reactions for which one of the markers is $H_2O_2$ production.

In order to do this, the day before measuring, 10-day-old plantlets were sprayed with a 2% solution of the composition with the formula (III) or water (control). The following day the production of $H_2O_2$ brought about either by osmotic shock (FIG. 3), or by chitin (FIG. 4) was measured in these plantlets, as described in Materials and Methods.

Figure 3:
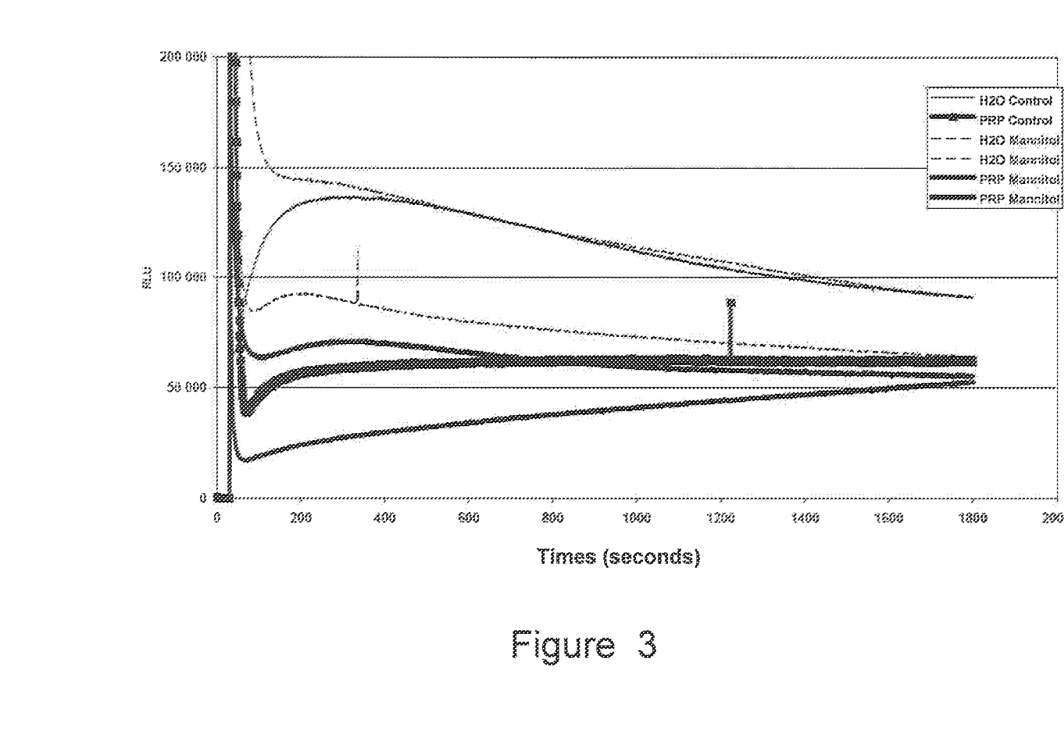
FIG. 3 shows the curves of hydrogen peroxide production ($H_2O_2$) in ten-day-old plantlets of *Arabidopsis thaliana*, induced by an osmotic shock, 24 hours after a pre-treatment of the plants in presence or absence of a composition with the formula (I). On the x-axis: the time in seconds. On the y-axis: Arbitrary (relative) luminescence units (RLU).
Figure 4:
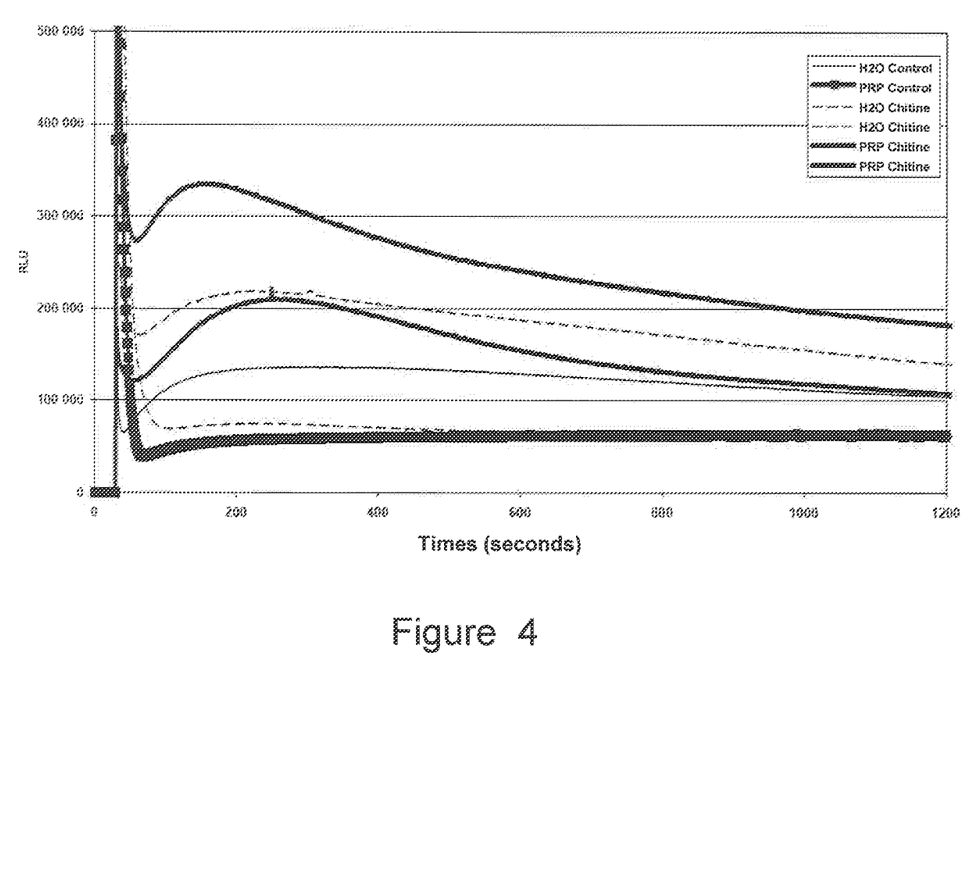
FIG. 4 shows the curves of hydrogen peroxide production ($H_2O_2$) in ten-day-old plantlets of *Arabidopsis thaliana*, induced by an elicitor shock by a chemical substance, chitin, 24 hours after a pre-treatment of the plants in presence or absence of a composition with the formula (I). On the x-axis: the time in seconds. On the y-axis: Arbitrary luminescence units (RLU).

The results are given in FIGS. 3 and 4. FIGS. 3 and 4 show the production of $H_2O_2$ in response to an osmotic shock (FIG. 3) or chitin (FIG. 4) in *Arabidopsis thaliana* plantlets pre-treated 24 hours earlier with water or the composition with the formula (III) at 2% (V/V).

In the response to mannitol which here mimics water stress, the intensity of responses observed was very variable. The level of intensity measured in plantlets pre-treated with the composition with the formula (III) is lower than that measured in plantlets pre-treated with water. However the mannitol does not bring about $H_2O_2$ production that is significantly different from that obtained by applying water instead of mannitol on plants previously sprayed with water ($H_2O$ control) or sprayed with a composition with the formula (III) (PRP).

Concerning the production of $H_2O_2$ brought about by chitin, it is noticed that in plantlets pre-treated with the composition with the formula (III), chitin brings about an $H_2O_2$ production that is 4 to 5 times higher than that of plantlets pre-treated with the composition with the formula (III) but incubated in the presence of water (PRP).

In the case of plantlets pre-treated with water and stimulated by chitin, the $H_2O_2$ production is not significantly different from the stimulation of the same plantlets by water ($H_2O$ control).

In conclusion, the results from example 4 show that pre-treatment of plantlets with the composition with the formula (III) has a stimulatory effect on $H_2O_2$ production in response to chitin. This indicates that plantlets pre-treated with the composition with the formula (III) have the ability to increase their defence reactions in response to a possible infection by a pathogenic agent containing or producing chitin such as fungi.

Example 5

Long Term Effect of a Composition with the Formula (I) on the Root Growth of *Arabidopsis thaliana* Plantlets Cultivated In Vitro In the study in Example 5, the *Arabidopsis thaliana* plantlets grown in agar dishes were sprayed either with a 2% (V/V) composition with the formula (III) or with water.

The next day, the plantlets were transferred into new dishes either on a normal medium, or on a stress inducing medium containing 100 mM NaCl or 350 mM mannitol.

The length of the tap root of the plantlets was then measured daily.

Figure 5:
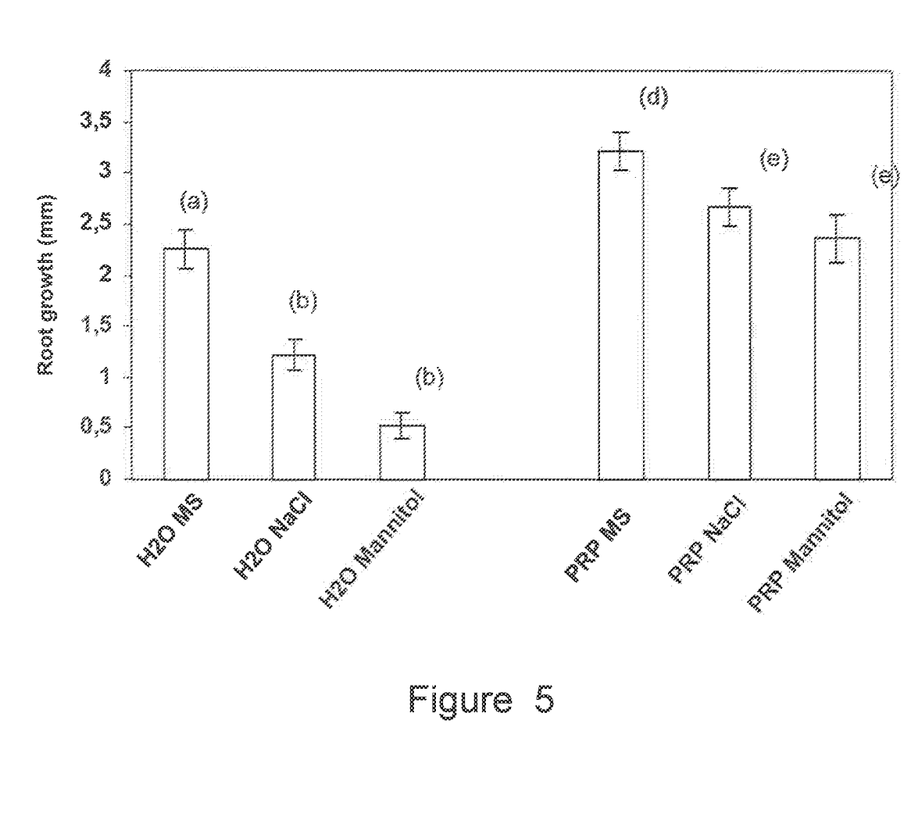

FIG. 5 presents the result of the measurements made 24 hours after the transfer, on 20 to 30 plantlets per batch. Despite a fairly large variability of length, a very significant ($p<0.01$) overall effect of the PRP-EPV product was observed on root growth. The increase in length of the tap root was greater in plantlets pre-treated with the composition with the formula (III) than in plantlets treated with H₂O, whether in control conditions (unstressed) or stressed conditions (NaCl or mannitol). On reading the graph it is apparent that the pre-treated plantlets resisted stress better than the control plantlets.

In conclusion, the results of example 5 show that the composition with the formula (III) has a positive effect on the growth of the tap root. This better growth including in stress conditions makes for better tolerance to water stress.

Example 6

Long Term Effect of a Composition with the Formula (I) on the Development of *Arabidopsis thaliana* Plantlets Cultivated in Pots To test the effect of the composition with the formula (III) on the resistance of *Arabidopsis thaliana* plantlets to various stresses, 10-day-old pot grown plants were treated by spraying with a 2% (V/V) composition with the formula (III) or water (controls), then watered on the following days with water containing 350 mM mannitol (osmotic stress simulating water stress) or 100 mM NaCl (salt stress), or left unwatered (water stress).

After 2 weeks of stress treatment the plantlets were watered normally with pure water.

It was observed that the treatments had the same effect on the development of the plantlets whether or not they had been treated with the composition with the formula (III).

On the contrary, it seems that after water stress by stopping watering, recovery of development after rehydration was improved in plantlets that had been pre-treated with a composition with the formula (III). This improved recovery was much more marked after 10 days of rehydration.

Conclusion: the results of Example 5 show that the pre-treatment with the composition with the formula (III) improves the recovery of plants after a high water stress (drying out of aerial parts).

The invention claimed is:

1. A liquid mineral composition for leaf spraying comprising the following formula (I):

| | |
|---|---|
| total ammoniacal nitrogen (N %) | 0.08% to 2% |
| potassium expressed as K₂O (%). | 3% to 6% |
| magnesium expressed as MgO (%) | 0.4% to 0.8% |
| sodium expressed as Na₂O (%) | 1% to 2% |
| calcium expressed as CaO (%) | 0% to 0.5% |
| total sulphates expressed as SO₃ (%) | 3% to 6% |
| total phosphorus expressed as P₂O₅ (%) | 0% |
| chlorides Cl (%) | 1% to 2% |
| bicarbonates (% of HCO₃) | 1.2% to 3.0% |
| boron (%) | 0.1 to 0.2% |
| copper (%) | 0.018% to 0.03% |
| manganese (%) | 0.00005% to 0.006% |
| iodine (%) | 0.02% to 0.04% |
| zinc (%) | 0.00005% to 0.006% |
| iron (mg/kg) | 0.0002 to 0.003 |
| water | water in a sufficient amount for 100% | the percentages consisting in percentages by weight compared to the total weight of the composition, for improving the adaptive response of plants to a change in environmental conditions.

2. The composition according to claim 1, wherein the adaptive response of plants to biotic or abiotic stress is improved.

3. The composition, according to claim 2, wherein the abiotic stress is selected from the group consisting of water stress, osmotic stress, heat stress, stress from overexposure to ionising or non-ionising radiation, nutritional deficiency, and stress caused by toxic substances.

4. The composition, according to claim 2, wherein the biotic stress is selected from the group consisting of bacteria, viruses, fungi, plant-eating organisms, insects and pathogens.

5. The composition according to claim 1, wherein the composition with the formula (I) also brings about an increase in the root development of plants.

6. The composition according to claim 1, wherein, the composition with the formula (I) is diluted in water or in an aqueous liquid in a proportion Composition (I): water or aqueous liquid ranging from 0.1:500 (V/V) to 10:500 (V/V).

7. The composition according to claim 6, wherein the composition with the formula (I) is diluted in water or in an aqueous liquid in a proportion composition (I): water or aqueous liquid ranging from 0.5:500 (V/V) to 2:500 (V/V).

8. A method of improving the adaptive response of plants to a change in environmental conditions, comprising leaf spraying of a liquid mineral composition comprising the following formula (I):

| | |
|---|---|
| total ammoniacal nitrogen (N %) | 0.08% to 2% |
| potassium expressed as K₂O (%). | 3% to 6% |
| magnesium expressed as MgO (%) | 0.4% to 0.8% |
| sodium expressed as Na₂O (%) | 1% to 2% |
| calcium expressed as CaO (%) | 0% to 0.5% |
| total sulphates expressed as SO₃ (%) | 3% to 6% |
| total phosphorus expressed as P₂O₅ (%) | 0% |
| chlorides Cl (%) | 1% to 2% |
| bicarbonates (% of HCO₃) | 1.2% to 3.0% |
| boron (%) | 0.1 to 0.2% |
| copper (%) | 0.018% to 0.03% |
| manganese (%) | 0.00005% to 0.006% |
| iodine (%) | 0.02% to 0.04% |
| zinc (%) | 0.00005% to 0.006% |
| iron (mg/kg) | 0.0002 to 0.003 |
| water | water in a sufficient amount for 100% | the percentages consisting in percentages by weight compared to the total weight of the composition.

9. The method according to claim 8, wherein the adaptive response of plants to biotic or abiotic stress is improved.

10. The method according to claim 9, wherein the abiotic stress is selected from the group consisting of water stress, osmotic stress, heat stress, stress from overexposure to ionising or non-ionising radiation, nutritional deficiency and stress caused by toxic substances.

11. The method according to claim 9, wherein the biotic stress is selected from the group consisting of bacteria, viruses, fungi, plant-eating organisms, insects and pathogens.

12. The method according to claim 8, wherein the composition with the formula (I) also brings about an increase in the root development of plants.

13. The method according to claim 8, wherein before leaf spraying, the composition with the formula (I) is diluted in water or in an aqueous liquid in a proportion Composition (I): water or aqueous liquid ranging from 0.1:500 (V/V) to 10:500 (V/V).

14. The method according to claim 13, wherein the composition with the formula (I) is diluted in water or in an aqueous liquid in a proportion composition (I): water or aqueous liquid ranging from 0.5:500 (V/V) to 2:500 (V/V).

* * * * *